United States Patent
Collier et al.

(10) Patent No.: US 11,192,837 B2
(45) Date of Patent: Dec. 7, 2021

(54) PROCESS FOR PRODUCING 2,3,3,3-TETRAFLUOROPROPENE, AND SYSTEM FOR CARRYING OUT SAME

(71) Applicant: ARKEMA FRANCE, Colombes (FR)

(72) Inventors: Bertrand Collier, Pierre-Benite (FR); Dominique Deur-Bert, Pierre-Benite (FR); Anne Pigamo, Pierre-Benite (FR); Audrey Riehl, Pierre-Benite (FR); Laurent Wendlinger, Pierre-Benite (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/973,518

(22) PCT Filed: Jun. 6, 2019

(86) PCT No.: PCT/FR2019/051356
§ 371 (c)(1),
(2) Date: Dec. 9, 2020

(87) PCT Pub. No.: WO2019/239040
PCT Pub. Date: Dec. 19, 2019

(65) Prior Publication Data
US 2021/0253501 A1    Aug. 19, 2021

(30) Foreign Application Priority Data

Jun. 12, 2018   (FR) ...................................... 1855108

(51) Int. Cl.
*C07C 17/20*        (2006.01)
*B01J 19/24*        (2006.01)
(Continued)

(52) U.S. Cl.
CPC ............. *C07C 17/206* (2013.01); *B01J 19/00* (2013.01); *B01J 19/0013* (2013.01); *B01J 19/24* (2013.01);
(Continued)

(58) Field of Classification Search
CPC ..... C07C 17/206; C07C 21/04; C07C 17/269; C07C 21/18; B01J 19/24; B01J 19/00;
(Continued)

(56) References Cited

U.S. PATENT DOCUMENTS

2009/0240090 A1    9/2009  Merkel et al.
2014/0121424 A1*   5/2014  Nose .................... C07C 17/206
                                                        570/160
(Continued)

FOREIGN PATENT DOCUMENTS

EP       1945600 B1      4/2009
WO    2008054781 A1      5/2008
WO    2013088195 A1      6/2013

OTHER PUBLICATIONS

ISA/EP; International Search Report and Written Opinion for International Patent Application No. PCT/FR2019/051356, dated Oct. 9, 2019, 13 pages.

*Primary Examiner* — Jafar F Parsa
(74) *Attorney, Agent, or Firm* — NK Patent Law (57) ABSTRACT

A process for producing 2,3,3,3-tetrafluoropropene comprises i) in a first adiabatic reactor comprising a fixed bed composed of an inlet and an outlet, bringing hydrofluoric acid into contact, in the gas phase with at least one chlorinated compound in order to produce a stream A comprising 2-chloro-3,3,3-trifluoropropene, ii) in a second adiabatic reactor comprising a fixed bed composed of an inlet and an outlet, bringing the stream A into contact, in the gas phase in the presence of a catalyst, with hydrofluoric acid, to produce a stream B comprising 2,3,3,3-tetrafluoropropene.

(Continued)

The temperature at the inlet of the fixed bed of one of said first or second reactors is between 300° C. and 400° C. The longitudinal temperature difference between the inlet and the outlet of the fixed bed of the reactor is less than 20° C.

12 Claims, 4 Drawing Sheets

(51) Int. Cl.
    *C07C 17/269*    (2006.01)
    *B01J 19/00*    (2006.01)
    *C07C 21/18*    (2006.01)
    *C07C 21/04*    (2006.01)

(52) U.S. Cl.
    CPC .......... *B01J 19/242* (2013.01); *B01J 19/2415* (2013.01); *C07C 17/269* (2013.01); *C07C 21/04* (2013.01); *C07C 21/18* (2013.01); *B01J 2219/00054* (2013.01); *B01J 2219/00063* (2013.01); *B01J 2219/00155* (2013.01)

(58) Field of Classification Search
    CPC ............... B01J 19/0016; B01J 19/2415; B01J 2219/00155; B01J 2219/00054; B01J 2219/00063
    See application file for complete search history.

(56) References Cited

U.S. PATENT DOCUMENTS

2014/0316171 A1   10/2014   Elsheikh et al.
2015/0203421 A1    7/2015   Takahashi et al.
2016/0347692 A1   12/2016   Tirtowidjojo et al.

\* cited by examiner

PROCESS FOR PRODUCING 2,3,3,3-TETRAFLUOROPROPENE, AND SYSTEM FOR CARRYING OUT SAME

CROSS-REFERENCE TO RELATED APPLICATIONS

This application is a U.S. National Stage application of International Patent Application No. PCT/FR2019/051356, filed on Jun. 6, 2019, which claims the benefit of French Patent Application No. 1855108, filed on Jun. 12, 2018.

TECHNICAL FIELD OF THE INVENTION

The present invention relates to the production of hydrofluoroolefins, in particular the present invention relates to the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds having a structure which is useful as functional materials, solvents, refrigerants, blowing agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes may be performed in the gas phase or in the liquid phase, in the absence or presence of a catalyst. For example, US 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2013/088195 also discloses a process for the preparation of 2,3,3,3-tetrafluoropropene from 1,1,1,2,3-pentachloropropane and/or 1,1,2,2,3-pentachloropropane, comprising the steps: (a) catalytic reaction of 1,1,1,2,3-pentachloropropane and/or 1,1,2,2,3-pentachloropropane with HF to give a reaction mixture comprising HCl, 2-chloro-3,3,3-trifluoropropene, 2,3,3,3-tetrafluoropropene, unreacted HF and possibly 1,1,1,2,2-pentafluoropropane; (b) separating the reaction mixture into a first stream comprising HCl and 2,3,3,3-tetrafluoropropene and a second stream comprising HF, 2-chloro-3,3,3-trifluoropropene and possibly 1,1,1,2,2-pentafluoropropane; (c) catalytic reaction of said second stream to give a reaction mixture comprising 2,3,3,3-tetrafluoropropene, HCl, unreacted 2-chloro-3,3,3-trifluoropropene, unreacted HF and possibly 1,1,1,2,2-pentafluoropropane; and (d) supplying the reaction mixture obtained in step c) directly to step a) without separation.

In processes for producing 2,3,3,3-tetrafluoropropene, the mastering and control of the reaction temperature is an important parameter which makes it possible to achieve the desired reaction kinetics, conversions and selectivities. This is also particularly recommended to avoid thermal decompositions of thermally sensitive compounds which can impact the activity of the catalyst through the formation of coke and thus considerably reduce the service life of the catalyst.

It is known from WO 2008/054781 that one temperature (300-350° C.) promotes formation of 1234yf, 245cb and 1233xf, while a higher temperature (350-450° C.) promotes formation of the isomers 1234ze, 245fa and 1233zd.

It is therefore important to master and control the temperature of the gases at the inlet of the reactors but also to master and control at all points of the catalytic mass, if there is one.

A multitubular reactor is by definition the ideal isothermal reactor for being able to control the reaction temperature and obtaining the most uniform reaction temperature possible since the catalyst is distributed in tubes and a fluid can circulate in the grille around the tubes to either remove reaction heat in the event of an exothermic reaction, or add heat in the event of an endothermic reaction. On the other hand, when large amounts of catalysts have to be used, the production of a multitubular reactor may prove to be impossible because it would take too many tubes and a homogeneous distribution of the gases in each of the tubes then proves to be very difficult to achieve. In addition, the maintenance of large multitubular reactors proves to be much more difficult and expensive; in particular, the catalyst change operations require lengthy immobilization of the reactor, both to drain the spent catalyst and to fill each tube extremely uniformly with new catalyst. This negative aspect will be reinforced when the service life of the catalyst is short.

Consequently, the use of an adiabatic fixed bed reactor is preferred. Nevertheless, this type of reactor does not exhibit heat exchange with an external environment by definition.

Indeed, the adiabatic reactor is characterized by a non-homogeneous temperature at any point of the fixed bed and thus, by a temperature gradient that is both radial and longitudinal, due to the reaction heats and thermal losses at the outer walls of the reactor.

Document US 2016/0347692 describes the implementation of a process for the radical production in a homogeneous gas phase of chlorinated or fluorinated propene in an adiabatic flow reactor controlling the turbulence of the streams entering the reactor.

There is nevertheless a need to improve the processes for producing 2,3,3,3-tetrafluoropropene in adiabatic reactors.

SUMMARY OF THE INVENTION

According to a first aspect, the present invention relates to a process for producing 2,3,3,3-tetrafluoropropene, comprising the steps:

i) in a first adiabatic reactor comprising a fixed bed composed of an inlet and an outlet, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream A comprising 2-chloro-3,3,3-trifluoropropene, ii) in a second adiabatic reactor comprising a fixed bed composed of an inlet and an outlet, bringing the stream A obtained in step i) into contact, in the gas phase in the presence of a catalyst, with hydrofluoric acid, in order to produce a stream B comprising 2,3,3,3-tetrafluoropropene; and characterized in that the temperature at the inlet of the fixed bed of one of said first or second reactors is between 300° C. and 400° C. and the longitudinal temperature difference between the inlet of the fixed bed and the outlet of the fixed bed of the reactor in question is less than 20° C.

The value of the longitudinal temperature difference is considered as an absolute value.

According to one preferred embodiment, the temperature at the inlet of the fixed bed of said first reactor is between 340° C. and 380° C. and the longitudinal temperature difference between the inlet of the fixed bed of said second reactor and the outlet of the fixed bed of said second reactor is less than 20° C.

According to one preferred embodiment, the temperature at the inlet of the fixed bed of said second reactor is between 330° C. and 360° C. and the longitudinal temperature difference between the inlet of the fixed bed of said first reactor and the outlet of the fixed bed of said first reactor is less than 20° C.

According to one preferred embodiment, the HF/2-chloro-3,3,3-trifluoropropene molar ratio in step ii) or the molar ratio between HF and said chlorinated compound in step i) or both is or are adjusted so as to keep the longitudinal temperature difference between the inlet of the fixed bed and the outlet of the fixed bed of the reactor in question less than 20° C.

According to one preferred embodiment, the HF/chlorinated compound molar ratio, in step i), is greater than or equal to 5, advantageously greater than or equal to 10, preferably greater than or equal to 12.

According to one preferred embodiment, the HF/2-chloro-3,3,3-trifluoropropene molar ratio, in step ii), is greater than or equal to 5, advantageously greater than or equal to 10, preferably greater than or equal to 12.

According to one preferred embodiment, the side walls of said first reactor and/or of said second reactor comprise an inner layer, an intermediate layer placed on said inner layer and an insulating layer placed on said intermediate layer; and the radial temperature difference between a point located at the center of the fixed bed of one of said first or second reactors and a point located in the radial plane at the level of the inner layer of the side wall of said reactor in question is less than 10° C. Said inner layer is that which is in contact with the reagents. The value of the radial temperature difference is considered as an absolute value.

According to one preferred embodiment, the side walls of said first reactor and/or of said second reactor comprise an inner layer, an intermediate layer placed on said inner layer and an insulating layer placed on said intermediate layer; said insulating layer being made of a heat-insulating material M2, the thickness of which ranges between 1 mm and 500 mm. Said inner layer is that which is in contact with the reaction mixture.

According to one preferred embodiment, the heat-insulating material M2 is selected from the group consisting of rock wool, glass wool, silicate fibers, calcium-magnesium silicates, calcium silicates, microporous insulators, cellular glass, expanded perlite and exfoliated vermiculite.

According to one preferred embodiment, the pressure at the inlet of said first reactor and at the inlet of said second reactor is between 3 and 15 bara.

According to another aspect, the present invention provides a facility for producing 2,3,3,3-tetrafluoropropene, comprising:

a first and a second adiabatic reactor, each of said first and second reactors comprising a bottom, a cover and side walls joining the bottom and the cover, at least one fixed bed and at least one rod supporting one or more temperature sensor(s); said bottom, said cover and said side walls each comprise at least an inner layer, an intermediate layer placed on said inner layer and an insulating layer placed around said intermediate layer; said inner layer is made of a material M1 comprising a nickel mass content of at least 30%; said intermediate layer is made of a material M1' comprising at least 70% by weight of iron; said insulating layer is made of a heat-insulating material M2 selected from the group consisting of rock wool, glass wool, silicate fibers, calcium-magnesium silicates, calcium silicates, microporous insulators, cellular glass, expanded perlite and exfoliated vermiculite; the length of said at least one rod supporting one or more temperature sensor(s) is at least equal to the height of said fixed bed; and said at least one rod comprises at least one temperature sensor placed in said fixed bed;

a system for feeding said first and second reactors with reaction stream;

a system for collecting and purifying the outlet stream from said second reactor;

optionally a system for collecting and/or purifying the outlet stream from said first reactor;

at least one conductivity meter capable of measuring the electrical conductivity of the reaction stream entering said first reactor.

According to one preferred embodiment, the system for feeding said first reactor with reaction stream comprises a supply line for hydrofluoric acid, at least one supply line for at least one chlorinated compound as defined above, and at least one device for mixing the hydrofluoric acid and said at least one chlorinated compound, and the system for feeding said second reactor with reaction stream comprises a supply line for hydrofluoric acid and at least one supply line for said stream A as defined above.

DETAILED DESCRIPTION OF THE INVENTION

The present invention relates to a process for producing 2,3,3,3-tetrafluoropropene (HFO-1234yf). More particularly, the invention relates to a two-step process for producing 2,3,3,3-tetrafluoropropene.

Preferably, said process for producing 2,3,3,3-tetrafluoropropene comprises the steps:

i) in a first adiabatic reactor comprising a fixed bed composed of an inlet and an outlet, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream A comprising 2-chloro-3,3,3-trifluoropropene, ii) in a second adiabatic reactor comprising a fixed bed composed of an inlet and an outlet, bringing the stream A obtained in step i) into contact, in the gas phase in the presence of a catalyst, with hydrofluoric acid in order to produce a stream B comprising 2,3,3,3-tetrafluoropropene.

Preferably, the temperature at the inlet of the fixed bed of one of said first or second reactors is between 300° C. and 400° C. and the longitudinal temperature difference between the inlet of the fixed bed and the outlet of the fixed bed of the reactor in question is less than 20° C.

Preferably, the temperature at the inlet of the fixed bed of said first reactor is between 330° C. and 400° C., preferably between 330° C. and 390° C., in particular between 340° C. and 380° C. In this step i), a temperature above 400° C. can render the catalyst irreversibly inactive, while a temperature below 300° C. prevents the fluorination reaction from being carried out.

Preferably, the temperature at the inlet of the fixed bed of said second reactor is between 320° C. and 400° C., preferably between 320° C. and 375° C., more preferentially between 320° C. and 360° C., in particular between 330° C. and 360° C. In this step ii), a temperature above 400° C. can render the catalyst irreversibly inactive, while a temperature below 300° C. prevents the fluorination reaction from being carried out.

Figure 2:
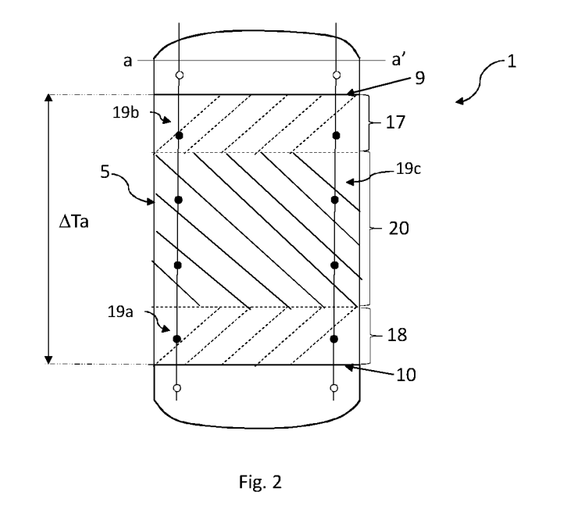
FIG. 2 schematically represents a view in longitudinal section of a reactor according to one particular embodiment of the present invention.

As mentioned above, in an adiabatic reactor, the temperature within the reactor, and in particular within the fixed bed, varies longitudinally, i.e. the temperature varies between the inlet of the reactor and the outlet of the reactor, in particular between the inlet of the fixed bed and the outlet of the fixed bed. FIG. 2 represents a schematic view in longitudinal section of a reactor 1 according to one particular embodiment of the present invention and comprising a fixed bed 5. The longitudinal temperature difference ΔTa is defined by the temperature difference between the inlet of the fixed bed 9 and the outlet of the fixed bed 10.

Preferably, the longitudinal temperature difference between the inlet of the fixed bed of said first reactor and the outlet of the fixed bed of said first reactor is less than 20° C., advantageously less than 19° C., preferably less than 18° C., more preferentially less than 17° C., in particular less than 16° C., more particularly less than 15° C., preferably less than 14° C., advantageously preferably less than 13° C., preferentially preferably less than 12° C., more preferentially preferably less than 11° C., particularly preferably less than 10° C.

Preferably, the longitudinal temperature difference between the inlet of the fixed bed of said second reactor and the outlet of the fixed bed of said second reactor is less than 20° C., advantageously less than 19° C., preferably less than 18° C., more preferentially less than 17° C., in particular less than 16° C., more particularly less than 15° C., preferably less than 14° C., advantageously preferably less than 13° C., preferentially preferably less than 12° C., more preferentially preferably less than 11° C., particularly preferably less than 10° C.

According to a preferred embodiment, step i) and step ii) are carried out in the presence of a catalyst, preferably a chromium-based catalyst. Preferably, the chromium-based catalyst may be a chromium oxide (for example $CrO_2$, $CrO_3$ or $Cr_2O_3$), a chromium oxyfluoride or a chromium fluoride (for example $CrF_3$) or a mixture thereof. The chromium oxyfluoride may have a fluorine content of between 1% and 60% by weight on the basis of the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight of fluorine on the basis of the total weight of chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1% and 10% by weight, based on the total weight of the catalyst. The catalyst may or may not be supported. A support, such as alumina, for example in its α form, activated alumina, aluminum halides ($AlF_3$, for example), aluminum oxyhalides, activated carbon, magnesium fluoride or graphite, can be used.

Preferably, the catalyst can a specific surface area of between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to a preferred embodiment, step i) is carried out at atmospheric pressure or at a pressure greater than atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara. Preferably, step i) is carried out at a pressure of between atmospheric pressure and 20 bara, preferably between 2 and 18 bara, more preferentially between 3 and 15 bara. Preferably, step i) of the present process is performed with a contact time of between 1 and 100 seconds, preferably between 2 and 75 seconds, in particular between 3 and 50 seconds. An oxidant, such as oxygen or chlorine, may be added during step i). The molar ratio of the oxidant to the hydrocarbon compound can be between 0.005 and 2, preferably between 0.01 and 1.5. The oxidant can be pure oxygen, air or a mixture of oxygen and nitrogen.

According to a preferred embodiment, step ii) is carried out at atmospheric pressure or at a pressure greater than atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara. Preferably, step ii) is carried out at a pressure of between atmospheric pressure and 20 bara, preferably between 2 and 18 bara, more preferentially between 3 and 15 bara. Preferably, step ii) of the present process is performed with a contact time of between 1 and 100 seconds, preferably between 2 and 75 seconds, in particular between 3 and 50 seconds. An oxidant, such as oxygen or chlorine, may be added during step ii). The molar ratio of the oxidant to the hydrocarbon compound can be between 0.005 and 2, preferably between 0.01 and 1.5. The oxidant can be pure oxygen, air or a mixture of oxygen and nitrogen.

Preferably, the stream A resulting from step i) feeds the second reactor without being purified prior to its injection into the latter.

Preferably, in step i), the HF/said at least one chlorinated compound molar ratio is greater than or equal to 5, advantageously greater than or equal to 10, preferably greater than or equal to 12. Advantageously, the HF/said at least one chlorinated compound molar ratio is between 12:1 and 150:1, preferably between 12:1 and 125:1, more preferentially between 12:1 and 100:1.

Preferably, in step ii), the HF/2-chloro-3,3,3-trifluoropropene molar ratio is greater than or equal to 5, advantageously greater than or equal to 10, preferably greater than or equal to 12. Advantageously, the HF/2-chloro-3,3,3-trifluoropropene molar ratio is between 12:1 and 150:1, preferably between 12:1 and 125:1, more preferentially between 12:1 and 100:1.

As mentioned above, in an adiabatic reactor, the temperature within the reactor, and in particular within the fixed bed, varies radially, i.e. the temperature varies between the center of the reactor and the side walls of the reactor located in the same plane, in particular between the center of the fixed bed and the side wall of the reactor located in the same plane.

The control of the radial temperature in the fixed bed can be carried out by insulating the side walls of said reactor with a heat-insulating material of a defined thickness. Thus, said side walls each comprise at least one inner layer and an insulating layer placed around said inner layer.

Figure 3:
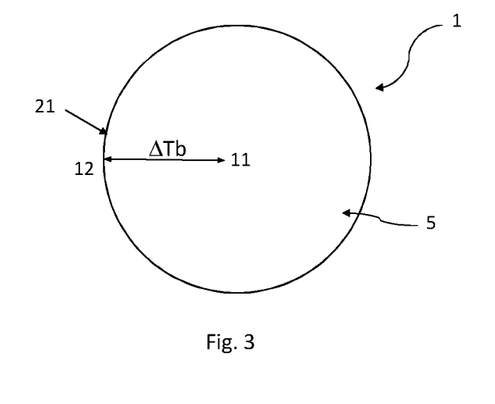
FIG. 3 schematically represents a view in transverse section of a reactor according to one particular embodiment of the present invention.
Figure 4:
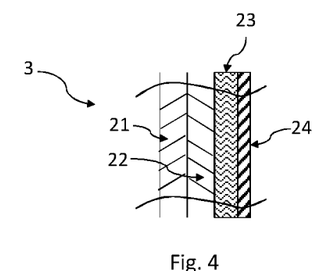
FIG. 4 schematically represents a sectional view of the side walls of a reactor according to one particular embodiment of the present invention.

FIG. 3 represents a transverse view along the sectional plane (a,a') of a reactor 1 according to one embodiment of the present invention and comprising a fixed bed 5. The side walls 3 of said first reactor and/or of said second reactor comprise an inner layer 21, an intermediate layer 22 placed on said inner layer 21 and an insulating layer 23 placed on said intermediate layer 22 (FIG. 4). The radial temperature difference ΔTb is defined by the difference between a point located at the center of the fixed bed 5 of one of said first or second reactors and a point 12 located in the radial plane at the level of the inner layer 21 of the side wall 3 of said reactor in question (FIG. 3).

Thus, the radial temperature difference between a point located at the center of the fixed bed of one of said first or second reactors and a point located in the radial plane at the level of the inner layer of the side wall of said reactor in question is less than 10° C., advantageously less than 9° C., preferably less than 8° C., more preferentially less than 7° C., in particular less than 6° C., more particularly less than 5° C.

Thus, the radial temperature difference between a point located at the center of the fixed bed of said first reactor and a point located in the radial plane at the level of the inner layer of the side wall of said first reactor is less than 10° C., advantageously less than 9° C., preferably less than 8° C., more preferentially less than 7° C., in particular less than 6° C., more particularly less than 5° C.

In addition, the radial temperature difference between a point located at the center of the fixed bed of said second reactor and a point located in the radial plane at the level of the inner layer of the side wall of said second reactor is less than 10° C., advantageously less than 9° C., preferably less than 8° C., more preferentially less than 7° C., in particular less than 6° C., more particularly less than 5° C.

According to one preferred embodiment, said inner layer has a thickness of between 0.01 and 20 mm. Preferably, said inner layer can have a thickness of between 0.05 and 15 mm, preferably between 0.1 and 10 mm, more preferentially between 0.1 and 5 mm.

Said inner layer can be made of a material M1 comprising a nickel mass content of at least 30%. Advantageously, the material M1 comprises at least 40% by weight of nickel on the basis of the total weight of the material M1. Preferably, the material M1 comprises at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M1. The material M1 may also comprise chromium in a content of less than 35% by weight on the basis of the total weight of the material M1, advantageously less than 30% by weight, preferably less than 20% by weight, more preferentially less than 15% by weight, in particular less than 10% by weight, more particularly less than 5% by weight on the basis of the total weight of the material M1. The material M1 may also comprise molybdenum in a content of less than 35% by weight on the basis of the total weight of the material M1, advantageously less than 30% by weight, preferably less than 20% by weight, more preferentially less than 15% by weight, in particular less than 10% by weight, more particularly less than 5% by weight on the basis of the total weight of the material M1. Preferably, the material M1 comprises at least 40% by weight of nickel on the basis of the total weight of the material M1, preferably at least 45% by weight of nickel, more preferentially at least 50% by weight of nickel, in particular at least 55% by weight of nickel, more particularly at least 60% by weight of nickel, favorably at least 65% by weight of nickel, more favorably at least 70% by weight of nickel on the basis of the total weight of the material M1; and less than 35% by weight of chromium, advantageously less than 30% by weight, preferably less than 20% by weight, more preferentially less than 15% by weight, in particular less than 10% by weight, more particularly less than 5% by weight of chromium on the basis of the total weight of the material M1; and less than 35% by weight of molybdenum, advantageously less than 30% by weight, preferably less than 20% by weight, more preferentially less than 15% by weight, in particular less than 10% by weight, more particularly less than 5% by weight of molybdenum on the basis of the total weight of the material M1. The material M1 may also comprise cobalt in a content of less than 10% by weight on the basis of the total weight of the material M1, advantageously less than 8% by weight, preferably less than 6% by weight, more preferentially less than 4% by weight, in particular less than 3% by weight, more particularly less than 2% by weight on the basis of the total weight of the material M1. The material M1 may also comprise tungsten in a content of less than 10% by weight on the basis of the total weight of the material M1, advantageously less than 9% by weight, preferably less than 8% by weight, more preferentially less than 7% by weight, in particular less than 6% by weight, more particularly less than 5% by weight on the basis of the total weight of the material M1. The material M1 may also comprise iron in a content of less than 25% by weight on the basis of the total weight of the material M1, advantageously less than 20% by weight, preferably less than 15% by weight, more preferentially less than 10% by weight, in particular less than 7% by weight, more particularly less than 5% by weight on the basis of the total weight of the material M1. The material M1 may also comprise manganese in a content of less than 5% by weight on the basis of the total weight of the alloy, advantageously less than 4% by weight, preferably less than 3% by weight, more preferentially less than 2% by weight, in particular less than 1% by weight, more particularly less than 0.5% by weight on the basis of the total weight of the material M1. The material M1 may also comprise copper in a content of less than 50% by weight, advantageously less than 45% by weight, preferably less than 40% by weight, more preferentially less than 35% by weight, in particular less than 30% by weight, more particularly less than 25% by weight of copper on the basis of the total weight of the material M1.

According to one preferred embodiment, said intermediate layer has a thickness of between 0.1 and 50 mm. Preferably, said intermediate layer may have a thickness of between 0.5 and 40 mm, preferably between 1 and 30 mm, more preferentially between 1 and 25 mm. According to one preferred embodiment, said intermediate layer 22 is placed between said inner layer 21, in contact with the reagents, and said insulating layer 23 (FIG. 4). Said intermediate layer 22 may be made of a material M1'. According to a preferred embodiment, the material M1' comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1'. The material M1' may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1'. More particularly, the material M1' may comprise between 0.01% and 0.2% by weight of carbon on the basis of the total weight of the material M1'. The material M1' may also comprise less than 2% by weight of molybdenum, advantageously less than 1.5% by weight, preferably less than 1.25% by weight, more preferentially less than 1% by weight of molybdenum on the basis of the total weight of the material M1'. More particularly, the material M1' may comprise between 0.1% and 1% by weight of molybdenum on the basis of the total weight of the material M1'. The material M1' may also comprise less than 5% by weight of chromium, advantageously less than 4% by weight, preferably less than 3% by weight, more preferentially less than 2% by weight, in particular less than 1% by weight of chromium on the basis of the total weight of the material M1'. More particularly, the material M1' may comprise between 0.5% and 2% by weight of chromium on the basis of the total weight of the material M1'. The material M1' may also comprise less than 2% by weight of silicon, advantageously less than 1.5% by weight, preferably less than 1.25% by weight, more preferentially less than 1% by weight of silicon on the basis of the total weight of the material M1'. More particularly, the material M1' may comprise between 0.1% and 1.5% by weight of silicon on the basis of the total weight of the material M1'. The material M1' may also comprise less than 2% by weight of manganese, advantageously less than 1.5% by weight, preferably less than 1.25% by weight, more preferentially less than 1% by weight of manganese on the basis of the total weight of the material M1'. More particularly, the material M1' may comprise between 0.1% and 1% by weight of manganese on the basis of the total weight of the material M1'.

Preferably, said insulating layer is made of a heat-insulating material M2. Said heat-insulating material M2 is selected from the group consisting of rock wool, glass wool, silicate fibers, calcium-magnesium silicates, calcium silicates, microporous insulators, cellular glass, expanded perlite and exfoliated vermiculite. The silicate fibers include, for example, aluminosilicate fibers.

In particular, the side walls of said first reactor comprise a layer made of a heat-insulating material M2, the thickness of which ranges between 1 mm and 500 mm, preferably between 5 mm and 400 mm.

In particular, the side walls of said second reactor comprise a layer made of a heat-insulating material M2, the thickness of which ranges between 1 mm and 500 mm, preferably between 5 mm and 400 mm.

According to a preferred embodiment of the invention, the pressure at the inlet of said first reactor of step i) is greater than the pressure at the inlet of said second reactor of step ii). Preferably, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 400 mbar to 2.0 bar, in particular from 750 mbar to 1.75 bar, more particularly from 1 to 1.5 bar.

According to a preferred embodiment, the pressure at the inlet of said first reactor is atmospheric pressure or a pressure greater than this; advantageously, the pressure at the inlet of said first reactor is greater than 1.5 bara, preferably greater than 2.0 bara, in particular greater than 2.5 bara, more particularly greater than 3.0 bara. Preferably, step i) is carried out at a pressure at the inlet of said first reactor of between atmospheric pressure and 20 bara, preferably between 2 and 18 bara, more preferentially between 3 and 15 bara. Thus, the pressure at the inlet of said second reactor can be less than atmospheric pressure. The pressure at the inlet of said second reactor can be greater than 1.5 bara while being less than that at the inlet of said first reactor, preferably greater than 2.0 bara while being less than that at the inlet of said first reactor, in particular greater than 2.5 bara while being less than that at the inlet of said first reactor, more particularly greater than 3.0 bara while being less than that at the inlet of said first reactor. Preferably, step ii) is carried out at a pressure between atmospheric pressure and 20 bara while being less than that at the inlet of said first reactor, preferably between 2 and 18 bara while being less than that at the inlet of said first reactor, more preferentially between 3 and 15 bara while being less than that at the inlet of said first reactor.

Step i) can be carried out at a temperature different from or equal to that of step ii). When step i) is carried out at a temperature different from that of step ii), step i) can be carried out at a temperature lower than that of step ii) or at a temperature greater than that of step ii).

According to a preferred embodiment, the hydrofluoric acid and said at least one chlorinated compound are brought into contact prior to the entry of these into said first reactor. The resulting mixture is the mixture C. Preferably, said at least one chlorinated compound is in the liquid state before it is brought into contact with the hydrofluoric acid. The latter is vaporized by mixing with the hydrofluoric acid. The resulting mixture C is then in gaseous form. In particular, the mixing between the hydrofluoric acid and said at least one chlorinated compound is carried out in a static mixer. Preferably, said at least one chlorinated compound is introduced into the static mixer via one or more spray nozzles. Said at least one chlorinated compound is thus sprayed in the form of droplets before being vaporized by mixing with the hydrofluoric acid, thus forming a mixture C in gaseous form. The spraying of said at least one chlorinated compound in the form of fine droplets makes it possible to ensure a more efficient vaporization of this compound. For example, the mean diameter of the droplets thus produced can be less than 500 μm.

Said mixture C can optionally be heated or cooled before it is introduced into said first reactor. This step can be carried out via a heat exchanger in order to control the temperature at the inlet of said first reactor. Said stream A obtained in step i) can be heated or cooled before it is introduced into the second reactor.

According to a preferred embodiment, said stream B comprises, apart from 2,3,3,3-tetrafluoropropene, HF, HCl, unreacted 2-chloro-3,3,3-trifluoropropene and optionally 1,1,1,2,2-pentafluoropropane. Preferably, the stream B is purified, preferably by distillation, in order to form a first stream comprising 2,3,3,3-tetrafluoropropene, HCl and optionally 1,1,1,2,2-pentafluoropropane and a second stream comprising HF and 2-chloro-3,3,3-trifluoropropene.

Preferably, said stream B is distilled under conditions which are sufficient to form said first stream comprising 2,3,3,3-tetrafluoropropene, HCl and optionally 1,1,1,2,2-pentafluoropropane and said second stream comprising HF and 2-chloro-3,3,3-trifluoropropene. In particular, the distillation can be carried out at a pressure of 2 to 6 bara, more particularly at a pressure of 3 to 5 bara. In particular, the temperature at the distillation column top is from −35° C. to 10° C., preferably from −20° C. to 0° C.

According to one preferred embodiment, said second stream is recycled to step i). Said second stream can optionally be purified, in particular by distillation, before being recycled to step i).

According to a preferred embodiment, said stream B obtained in step ii) is cooled prior to the abovementioned purification. In particular, said stream B obtained in step ii) is cooled to a temperature of less than 100° C., then distilled in order to form said first stream comprising 2,3,3,3-tetrafluoropropene, HCl and optionally 1,1,1,2,2-pentafluoropropane and said second stream comprising HF and 2-chloro-3,3,3-trifluoropropene; the temperature at the distillation column top is from −35° C. to 10° C. and the distillation is carried out at a pressure from 2 to 6 bara; said second stream obtained at the distillation column bottom is recycled to step i). Said stream B can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the stream of products obtained to such temperatures facilitates the subsequent distillation. The cooling of said stream B can be carried out by virtue of one or a plurality of heat exchangers. The cooling of said stream B can be carried out by passing the latter through one, two, three, four, five, six, seven, eight, nine or ten heat exchangers; preferably, the number of heat exchangers is between 2 and 8, in particular between 3 and 7.

Preferably, the process according to the present invention is carried out continuously.

Preferably, the process is carried out continuously and in the gas phase.

Preferably, said second stream that has been recycled to step i) has an electrical conductivity of less than 15 mS/cm, advantageously less than 14 mS/cm, preferably less than 13 mS/cm, more preferentially less than 12 mS/cm, in particular less than 11 mS/cm, more particularly less than 10 mS/cm, more preferably less than 9 mS/cm, advantageously preferably less than 8 mS/cm, preferentially preferably less than 7 mS/cm, more preferentially preferably less than 6 mS/cm, particularly preferably less than 5 mS/cm. Preferably, step i) and/or step ii) is carried out in the presence of hydrofluoric acid having an electrical conductivity of less than 10 mS/cm, preferably less than 5 mS/cm.

The electrical conductivity of said second stream is measured prior to being introduced into the first reactor. Preferably, the electrical conductivity is measured when said second stream is in liquid form. The present process can therefore comprise a step of heating said second stream prior to the implementation of step i) for providing said second stream in gaseous form. The electrical conductivity is measured at ambient temperature. The electrical conductivity is measured using an inductive conductivity measurement cell according to the practice known to those skilled in the art. Preferably, the measurement cell is coated with a material resistant to a corrosive medium, in particular resistant to hydrofluoric acid. The electrical conductivity of a stream can be reduced, in order to achieve a conductivity of less than 15 mS/cm, by reducing the concentration of electrolyte possibly present in the stream according to techniques known to those skilled in the art (distillation, cooling and separation by settling, passage through 3 to 5 Å molecular sieves or zeolites). Such an electrical conductivity makes it possible to improve the conversion and/or the selectivity of the reaction.

Figure 1:
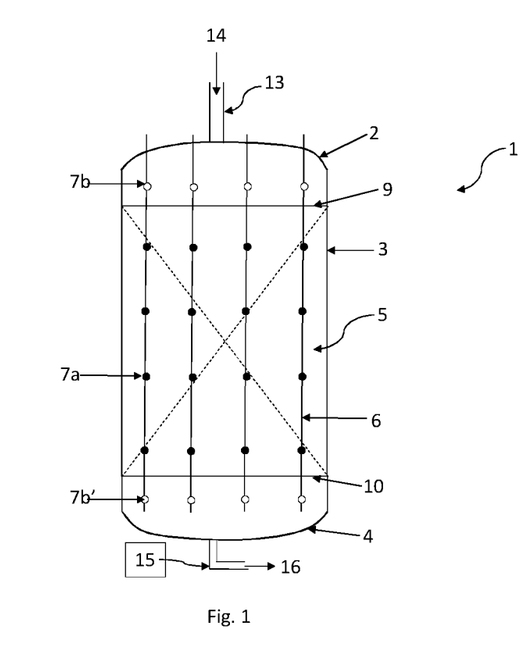
FIG. 1 schematically represents a reactor according to one particular embodiment of the present invention.

According to a second aspect of the present invention, an adiabatic reactor 1 is provided. Preferably, said reactor 1 comprises a bottom 4, a cover 2 and side walls 3 joining the bottom 4 and the cover 2, at least one fixed bed 5 and at least one rod 6 supporting one or more temperature sensors 7a, 7b (FIG. 1).

Preferably, said bottom 4, said cover 2 and said side walls 3 each comprise at least one inner layer 21, an intermediate layer 22 placed on said inner layer and an insulating layer 23 placed around said intermediate layer. Said inner layer 21, intermediate layer 22 and insulating layer 23 are respectively made of a material M1, M1' and M2 as described above. According to one preferred embodiment, said insulating layer 23 may be covered by a base layer 24. Thus, said insulating layer 23 is placed between said intermediate layer 22 and said base layer 24 (FIG. 4). Said base layer 24 may be made of a material M3. Said material M3 can be a metallic coating made with sheets of aluminum, stainless steel or galvanized steel. Preferably, said base layer has a thickness of between 0.2 mm and 2 mm. Said inner layer 21, said intermediate layer 22, said insulating layer 23 and said base layer 22 can be placed one on top of the other according to techniques well known to those skilled in the art.

Preferably, the length of said at least one rod 6 is at least equal to the height of said fixed bed 5. In particular, said at least one rod 6 comprises at least one temperature sensor or at least two temperature sensors or at least 3 temperature sensors, advantageously at least 5 temperature sensors, preferably at least 7 temperature sensors, in particular at least 10 temperature sensors, preferably at least 12 temperature sensors, preferentially preferably at least 15 temperature sensors. Preferably, at least one of said one or more temperature sensors, supported by said at least one rod, is placed in said fixed bed 5. In particular, at least two or three or four or five or six or seven temperature sensors, supported by said at least one rod, are arranged in said fixed bed 5. Preferably, each rod 6 can comprise either an identical number or a different number of temperature sensors. In particular, each rod can comprise a temperature sensor in the headspace and/or in the bottom of the reactor (FIG. 1, reference 7b and 7b'). Likewise, the temperature sensors 7a, 7b can be distributed equidistantly or in a more targeted manner as required for controlling the temperature profile in the fixed bed. Preferably, said reactor can comprise at least two rods 6, more preferentially at least three rods 6, in particular at least four rods 6. In particular, said reactor may comprise between 1 and 20 rods 6, advantageously between 2 and 15 rods 6, preferably between 3 and 10 rods 6.

Preferably, the reactor 1 is fed with hydrocarbon compound 14 via feed lines 13. The reactor also comprises effluent or outlet lines 15 for removing the reaction mixture 16 from the reactor (FIG. 1). Preferably, the feed or outlet lines of the reactor are made of material capable of also resisting corrosion, for example made of the material M1 covered with a layer of material M2 and a base layer made of a material M3. The feed lines may be of tubular shape. Alternatively, the feed or outlet lines may comprise an inner layer, preferably made of a material M1 as described above, an insulating layer, preferably made of a material M2 as described above, and a base layer, preferably made of a material M3 as described above. The reactor also comprises one or more dephlegmator(s), one or more dip tube(s), one or more device(s) for introducing the raw materials, and one or more grating(s) for supporting and retaining the catalyst. Said one or more dephlegmator(s) and/or said one or more dip tube(s) and/or said one or more device(s) for introducing the raw materials and/or said one or more grating(s) for supporting and retaining the catalyst may comprise an inner layer, preferably made of a material M1 as described above.

Preferably, the fixed bed 5 comprises a catalyst or an inert solid or both. The inert solid can be corundum, silicon carbide, quartz balls or rings, a metallic packing made of a metal M1 as defined in the present application or nickel balls. Preferably, when the fixed bed 5 comprises a catalyst, the inert solid is placed in the upper part 17 and the lower part 18 of the fixed bed 5, said catalyst 19c being located between the layers of inert solid 19a and 19b, in the central part 20 of the fixed bed 5. In an alternative embodiment, when the fixed bed 5 comprises a catalyst, inert solid is placed in the upper part 17 or in the lower part 18 of the fixed bed 5. In an alternative embodiment, when the fixed bed 5 comprises a catalyst, no layer of inert solid is placed in the fixed bed. In an alternative embodiment, wherein the reactor does not contain a catalyst, the lower part 18, the central part 20 and the upper part 17 of the fixed bed 5 may contain only inert solid. This alternative embodiment can be implemented when, for example, step i) of the process according to the present invention is carried out in the absence of a catalyst. In this case, the inert solid makes it possible to improve the distribution of gases inside the reactor. Preferably, the inert solid is corundum or nickel beads.

Preferably, the fixed bed 5 contains a catalyst layer 19c in its central part 20. In one preferred embodiment, the catalyst is distributed homogeneously in the fixed bed. The homogeneous distribution of the catalyst in the fixed bed makes it possible to minimize disruptions in the gas flow and to avoid hot spots within the catalyst layer. The presence of hot spots can lead to irreversible crystallization of the catalyst causing deactivation thereof. The loading of the fixed bed is carried out according to the specific method of dense loading of the catalyst. This method is known to those skilled in the art. It makes it possible to obtain an optimal distribution of the catalyst inside the reactor by avoiding channeling during the reaction and the attrition of the catalyst. In general, the apparent density by weight of the catalyst in the fixed bed is greater than the theoretical density by weight thereof. The apparent density by weight is determined according to ASTM D1895.

Preferably, said reactor is a gas-phase fluorination reactor.

The present invention makes it possible to implement a process for producing 2,3,3,3-tetrafluoropropene with a larger amount of catalyst. In addition, the radial and longitudinal mastering and control of the temperature make it possible to maintain reaction conversion and selectivity.

Figure 5:
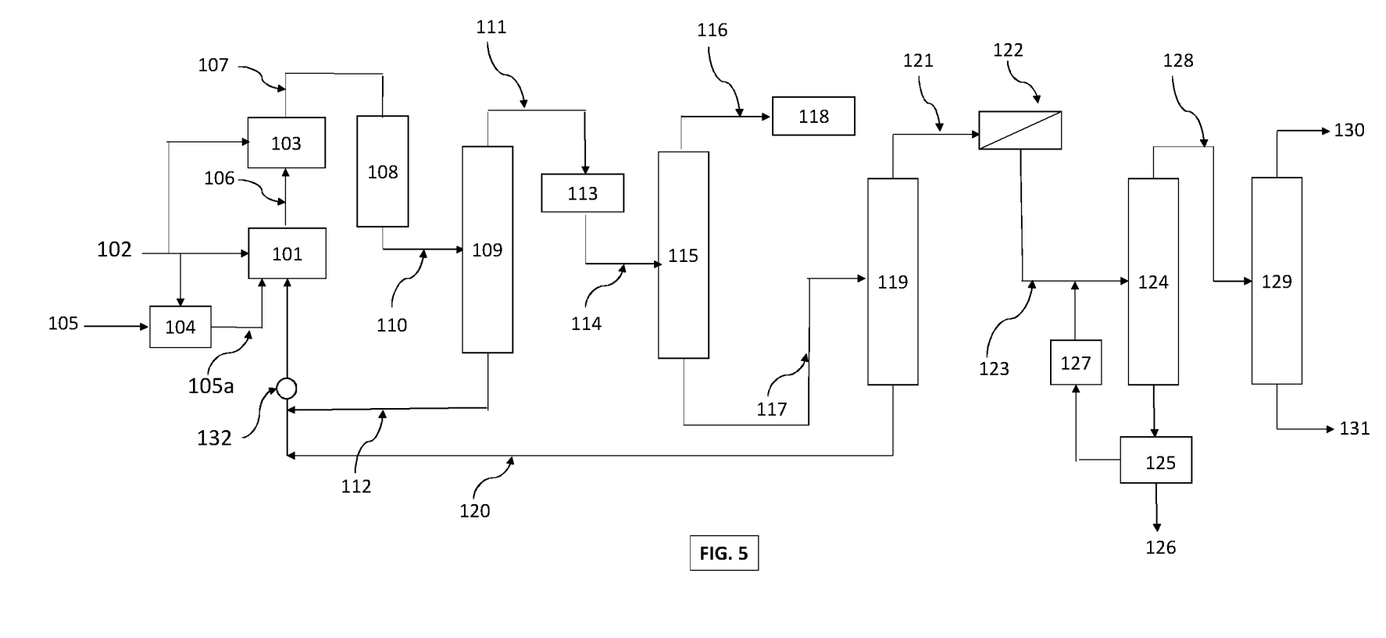
FIG. 5 schematically represents a facility for producing 2,3,3,3-tetrafluoropropene according to one particular embodiment of the present invention.

According to a third aspect of the invention, a facility for producing 2,3,3,3-tetrafluoropropene is provided. Preferably, the facility comprises a first adiabatic reactor 101 according to the present invention; a second adiabatic reactor 103 according to the present invention; a system for feeding said first and second reactors with reaction stream; a system for collecting and purifying the outlet stream from said second reactor and optionally a system for collecting and/or purifying the outlet stream from said first reactor.

Preferably, said facility also comprises a heat exchanger fed with the outlet stream 107 and connected to a first distillation column 109. Preferably, said facility also comprises a compressor 113 fed with the stream coming from said first distillation column 109. Preferably, said facility comprises a second distillation column 115 fed with a stream coming from the compressor 113. Said second distillation column 115 aims to remove all or a portion of the HCl present in the stream conveyed to it. Said facility may also comprise a plurality of other distillation columns for purifying the 2,3,3,3-tetrafluoropropene and removing impurities.

A facility according to one particular embodiment of the present invention is illustrated in FIG. 5 and described below.

The system for feeding said first reactor with reaction stream comprises a supply line for hydrofluoric acid 102 and at least one supply line for said chlorinated compound 105. The facility also comprises a device 104 for mixing the hydrofluoric acid and said chlorinated compound. The mixing device is preferably a static mixer. Thus, the hydrofluoric acid and said at least one chlorinated compound are mixed, pulverized and vaporized in said mixing device 104 before being introduced into said first reactor 101 via the pipe 105a. The system for feeding said second reactor with reaction stream comprises a supply line for hydrofluoric acid 102, and at least one supply line 106 for the 2-chloro-3,3,3-trifluoropropene coming from and produced by the first reactor 101. Preferably, the outlet stream 107 from said second reactor that is collected and purified comprises 2-chloro-3,3,3-trifluoropropene, HF, HCl, 2,3,3,3-tetrafluoropropene and optionally 1,1,1,2,2-pentafluoropropane. The heat exchanger 108 is able to cool the outlet stream 107 coming from said second reactor 103 to form a cooled stream. The outlet stream 107 is conveyed to a cooling device 108 to be cooled to a temperature of 0° C. to 70° C. before being introduced into a distillation column 109 via a pipe 110. The distillation column 109 is configured so as to allow separation between, on the one hand, hydrochloric acid, 2,3,3,3-tetrafluoropropene and optionally 1,1,1,2,2-pentafluoropropane, and, on the other hand, hydrofluoric acid and 2-chloro-3,3,3-trifluoropropene. The stream of HF and of 2-chloro-3,3,3-trifluoropropene is recovered at the bottom of distillation column 109 and is recycled to the first reactor 101 via the pipe 112. The stream comprising 2,3,3,3-tetrafluoropropene and hydrochloric acid and optionally 1,1,1,2,2-pentafluoropropane is recovered at the top of distillation column 109 to be conveyed via a pipe 111 to a compressor 113. The compressor makes it possible to compress the stream comprising 2,3,3,3-tetrafluoropropene and hydrochloric acid to a pressure of between 10 and 25 bara. The stream thus compressed is conveyed by the pipe 114 to a second distillation column 115. Said distillation column is configured so as to separate, on one hand, 2,3,3,3-tetrafluoropropene and optionally 1,1,1,2,2-pentafluoropropane and, on the other hand, hydrochloric acid. The hydrochloric acid is recovered at the top of the distillation column 115 to be conveyed to a purification device 118 by the pipe 116. The hydrochloric acid purification device 118 is a device known from the prior art, for example from WO 2015/079137. The 2,3,3,3-tetrafluoropropene and optionally 1,1,1,2,2-pentafluoropropane are recovered at the bottom of distillation column 115 to be conveyed via the pipe 117 to a third distillation column 119. The distillation column 119 is intended to separate the 2,3,3,3-tetrafluoropropene from the 1,1,1,2,2-pentafluoropropane possibly present in the outlet stream 107. The 2,3,3,3-tetrafluoropropene is recovered at the top of the distillation column to be conveyed to a purification device by the pipe 121. The 1,1,1,2,2-pentafluoropropane recovered at the bottom of the distillation column is recycled to the first reactor 101 by the pipe 120. The purification device comprises in particular a device for removing the HF 122 and one or more distillation columns capable of purifying out of the stream comprising 2,3,3,3-tetrafluoropropene any impurities that it could contain, such as for example residual 1,1,1,2,2-pentafluoropropane and/or 1,3,3,3-tetrafluoropropene. The device for removing HF 122 removes the residual HF which can be recycled to the first reactor 101 or the second reactor 103 (not shown). The device for removing HF 122 may be capable of allowing decanting of the HF or absorption of the HF. The stream comprising 2,3,3,3-tetrafluoropropene is conveyed to a distillation column 124 by the pipe 123. The distillation column 124 is an extractive distillation column. An extraction agent 127 is added to the stream comprising 2,3,3,3-tetrafluoropropene. The extractive distillation column 124 makes it possible to remove any impurities possibly present in the stream comprising 2,3,3,3-tetrafluoropropene. These impurities can comprise 1,3,3,3-tetrafluoropropene or 1,1,1,2,2-pentafluoropropane. A stream comprising 2,3,3,3-tetrafluoropropene is recovered at the top of distillation column 124 and is conveyed by a pipe 128 to a distillation column 129. The distillation column 129 can make it possible to separate the 2,3,3,3-tetrafluoropropene from residual 1,1,1,2,2-pentafluoropropane. A stream 130 comprising 2,3,3,3-tetrafluoropropene is recovered at the top of the distillation column. A stream 131 comprising the 1,1,1,2,2-pentafluoropropane is recovered at the bottom of the distillation column; the latter being able to be recycled to the first reactor 101 (not shown). The stream 125 recovered at the bottom of the distillation column 124 comprises the organic extraction agent and the 1,3,3,3-tetrafluoropropene. These compounds are separated, for example by distillation, to form a stream 126 comprising 1,3,3,3-tetrafluoropropene. The organic extraction agent is for its part recycled to 127. As mentioned above, the stream coming from the bottom of the distillation column 119 and the stream coming from the bottom of the distillation column 109 are conveyed to the first reactor 101 respectively by the pipes 120 and 112. The two streams can be mixed before being introduced into said first reactor 101 or before being introduced into the mixing device 104. Furthermore, before being introduced into said first reactor 101, the electrical conductivity of the two streams or of the mixture thereof is measured by the conductivity meter 132.

The invention claimed is:

1. A process for producing 2,3,3,3-tetrafluoropropene, comprising the steps:
   i. in a first adiabatic reactor comprising a fixed bed composed of an inlet and an outlet, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream A comprising 2-chloro-3,3,3-trifluoropropene,
   ii. in a second adiabatic reactor comprising a catalyst bed composed of an inlet and an outlet, bringing the stream A obtained in step i) into contact, in the gas phase in the presence of a catalyst, with hydrofluoric acid, in order to produce a stream B comprising 2,3,3,3-tetrafluoropropene; wherein
   a temperature at the inlet of the fixed bed of one of said first or second reactors is between 300° C. and 400° C. and a longitudinal temperature difference between the inlet of the fixed bed and the outlet of the fixed bed of the reactor in question is less than 20° C.

2. The process as claimed in claim 1, wherein the temperature at the inlet of the fixed bed of said first reactor is between 340° C. and 380° C. and a longitudinal temperature difference between the inlet of the fixed bed of said second reactor and the outlet of the fixed bed of said second reactor is less than 20° C.

3. The process as claimed in claim 1, wherein the temperature at the inlet of the fixed bed of said second reactor is between 330° C. and 360° C. and a longitudinal temperature difference between the inlet of the fixed bed of said first reactor and the outlet of the fixed bed of said first reactor is less than 20° C.

4. The process as claimed in claim 1, wherein a HF/2-chloro-3,3,3-trifluoropropene molar ratio in step ii) or a molar ratio between HF and said at least one chlorinated compound in step i) or both is/are adjusted so as to keep a longitudinal temperature difference between the inlet of the fixed bed and the outlet of the fixed bed of the reactor in question less than 20° C.

5. The process as claimed in claim 1, wherein the HF/at least one chlorinated compound molar ratio, in step i), is greater than or equal to 5.

6. The process as claimed in claim 1, wherein the HF/2-chloro-3,3,3-trifluoropropene molar ratio, in step ii), is greater than or equal to 5.

7. The process as claimed in claim 1, wherein said first and/or second reactors comprise side walls, said side walls comprising an inner layer, an intermediate layer placed on said inner layer and an insulating layer placed on said intermediate layer; and wherein a radial temperature difference between a point located at a center of the fixed bed of one of said first or second reactors and a point located in a radial plane at a level of the inner layer of the side wall of said reactor in question is less than 10° C.

8. The process as claimed in claim 1, wherein said first and/or second reactors comprise side walls, said side walls comprising an inner layer, an intermediate layer placed on said inner layer and an insulating layer placed on said intermediate layer; said insulating layer being made of a heat-insulating material M2, the thickness of which ranges between 1 mm and 500 mm.

9. The process as claimed in claim 8, wherein the heat-insulating material M2 is selected from the group consisting of rock wool, glass wool, silicate fibers, calcium-magnesium silicates, calcium silicates, microporous insulators, cellular glass, expanded perlite, and exfoliated vermiculite.

10. The process as claimed in claim 1, wherein a pressure at the inlet of said first reactor and/or at the inlet of said second reactor is between 3 and 15 bara.

11. A facility for producing 2,3,3,3-tetrafluoropropene, comprising:
- a first and a second adiabatic reactor, each of said first and second reactors comprising a bottom, a cover and side walls joining the bottom and the cover, at least one fixed bed and at least one rod supporting one or more temperature sensor(s); said bottom, said cover and said side walls each comprise at least an inner layer, an intermediate layer placed on said inner layer and an insulating layer placed around said intermediate layer; said inner layer is made of a material M1 comprising a nickel mass content of at least 30%; said intermediate layer is made of a material M1' comprising at least 70% by weight of iron; said insulating layer is made of a heat-insulating material M2 selected from the group consisting of rock wool, glass wool, silicate fibers, calcium-magnesium silicates, calcium silicates, microporous insulators, cellular glass, expanded perlite and exfoliated vermiculite; the length of said at least one rod supporting the one or more temperature sensor(s) is at least equal to the height of said fixed bed; and said at least one rod comprises at least one of the one or more temperature sensors placed in said fixed bed;
- a system for feeding said first and second reactors with a reaction stream;
- a system for collecting and purifying an outlet stream from said second reactor;
- optionally a system for collecting and/or purifying an outlet stream from said first reactor;
- at least one conductivity meter capable of measuring the electrical conductivity of the reaction stream entering said first reactor.

12. The facility as claimed in claim 11, wherein:
the system for feeding said first reactor with the reaction stream comprises a supply line for hydrofluoric acid, at least one supply line for at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, and at least one device for mixing hydrofluoric acid and said at least one chlorinated compound, and
the system for feeding said second reactor with the reaction stream comprises a supply line for hydrofluoric acid and at least one supply line for a stream A comprising 2-chloro-3,3,3-trifluoropropene.

* * * * *